(12) United States Patent
Schiene et al.

(10) Patent No.: US 7,887,223 B2
(45) Date of Patent: Feb. 15, 2011

(54) LAMP-BALLAST-SYSTEM WITH INTEGRATED COOLING CIRCUIT

(75) Inventors: Wolfgang Schiene, Wurselen (DE); Georg Greuel, Roetgen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 893 days.

(21) Appl. No.: 11/719,861

(22) PCT Filed: Nov. 21, 2005

(86) PCT No.: PCT/IB2005/053827
§ 371 (c)(1),
(2), (4) Date: May 22, 2007

(87) PCT Pub. No.: WO2006/056921
PCT Pub. Date: Jun. 1, 2006

(65) Prior Publication Data
US 2008/0290776 A1    Nov. 27, 2008

(30) Foreign Application Priority Data
Nov. 25, 2004  (EP)  .................................. 04106059

(51) Int. Cl.
*B60Q 1/00* (2006.01)
(52) U.S. Cl. ........................ 362/547; 362/546; 362/218; 362/651; 362/657
(58) Field of Classification Search .................. 362/651, 362/652, 657, 656, 647, 658, 655, 640, 259, 362/263, 264, 294, 546, 547–549
See application file for complete search history.

(56) References Cited

U.S. PATENT DOCUMENTS

| 3,816,784 | A |   | 6/1974 | Weninger |
|---|---|---|---|---|
| 5,738,438 | A | * | 4/1998 | Hesprich ..................... 362/374 |
| 5,831,394 | A |   | 11/1998 | Huber et al. |
| 5,952,792 | A |   | 9/1999 | Borowiec et al. |
| 6,201,355 | B1 |  | 3/2001 | Morgan et al. |
| 6,353,294 | B1 |  | 3/2002 | Wammes et al. |
| 2002/0068017 | A1 | | 6/2002 | Naatz et al. |
| 2002/0089275 | A1 | | 7/2002 | Falkenstein |
| 2002/0158589 | A1 | | 10/2002 | Hitzschke et al. |
| 2003/0094909 | A1 | | 5/2003 | Hishinuma |
| 2003/0122092 | A1 | | 7/2003 | Sarchese et al. |

FOREIGN PATENT DOCUMENTS

| EP | 0848411 |     | 6/1998 |
|----|---------|-----|--------|
| EP | 1072558 | A1  | 1/2001 |
| WO | WO0230828 | A2 | 4/2002 |
| WO | WO2004068031 | A1 | 8/2004 |

\* cited by examiner

*Primary Examiner*—Tuyet Thi Vo

(57) ABSTRACT

The subject of the present invention is a lamp-ballast-system (1), especially a dielectric barrier discharge (DBD-) lamp-ballast-system for generating and/or emitting a radiation of ultraviolet (UV-)-light comprising: a lamp (2) having means for electrical contacting and a ballast (3) having a housing (4) accommodating at least a high-voltage part and a lamp support, connectable to and supplying the DBD-lamp (2) at least with electricity, whereby the electrical connection (5) between the DBD-lamp (2) and the ballast (3) is arranged cable-free.

6 Claims, 1 Drawing Sheet

LAMP-BALLAST-SYSTEM WITH INTEGRATED COOLING CIRCUIT

The present invention relates to a lamp-ballast-system, especially to a dielectric barrier discharge (DBD-) lamp-ballast-system for generating and/or emitting a radiation of ultraviolet (UV-)-light comprising: a DBD-lamp having means for electrical contacting and/or electrical supply, and a ballast having a housing accommodating at least a high-voltage part and a lamp support, connectable to and supplying the DBD-lamp at least with electricity.

Such well known (dielectric barrier discharge) lamp-ballast-systems are generally known and are used in a wide area of applications, where light waves of a certain wavelength have to be generated for a variety of purposes. Some applications are for example generating UV light with wavelengths of about 180 nm to 380 nm for industrial purposes such as waste water treatment, disinfections of drinking water, dechlorination or producing of ultra pure water. Such (dielectric barrier discharge) lamp-ballast-systems are generally known as mentioned before.

This well known lamp-ballast-systems are used in case of a DBD-lamp-ballast-system for example in flat lamps for liquid crystal display (LCD) backlighting, as cylindrical lamps for photocopiers, and as co-axial lamps for surface and water treatment purposes. All of these (DBD-) lamp-ballast-systems comprise a (DBD-) lamp and a ballast, whereby (DBD-) lamp and ballast are arranged separated from each other and the electrical connection between (DBD-) lamp and ballast is arranged via electric lines or cabling.

Further it is well known, to install a cooling circuit with such lamp-ballast-systems, whereby the cooling circuit leads a cooling agent, which is brought to the lamp and/or the ballast via external lines.

US 2002/0158589 A1 shows an operating method for a discharge lamp and an illuminating system having a discharge lamp with a dielectric layer between at least one electrode and a discharge medium and with a ballast having a power supplied primary circuit, a secondary circuit into which the discharge lamp is switched, and a transformer connecting the primary circuit to the secondary circuit, whereby the length of the electric lines between the ballast and the discharge lamp is at most 10 cm and/or whereby the ballast is incorporated in a base housing of the discharge lamp.

One drawback of this illuminating system is that although the cabling length is limited to at most 10 cm still cabling is necessary. That means that unwanted losses e.g. in form of idle power losses or effective power losses due to the cabling exists, because of the electrical impedance of the cabling. Furthermore electromagnetic disturbance will be caused due to the cabling.

Typically, DBD-lamps are operated using high voltages, which could reach the range of several kV. Hence, there is a risk of latent exposure and the efforts for reliable operation are high.

Additionally cabling which fulfil the efforts for reliable operation, that is suitable electrical isolation and low capacity by having simultaneously shielding against interfering field emission are cost-intensive. Especially in applications where several DBD-lamp-ballast-systems are needed, suitable cabling makes a high part of the effort for using the application.

For high power lamp-ballast systems cooling, either in form of natural convection, forced convection, and/or liquid cooling is necessary.

US 2002/0068017 A1 shows a system for the measurement of the total organic carbon content of a sample of water comprising a cell of material capable of containing plasma, said cell defining an interior volume for receiving an oxidant gas and said sample, and being provided with at least one inlet and one outlet port; first and second electrodes disposed on opposite sides of said cell; a high voltage power supply connected across said first and second electrodes, whereby a cooling device, that is a thermoelectric cooler or a forced air cooler, is also attached to the ground electrode to maintain it at a moderate temperature during operation and/or a high voltage electrode of the same construction and dimensions, that is attached in the same way and may similarly be supplied with a cooling device.

One drawback of this system is that due to the local separation of ballast and DBD-lamp separate cooling devices for ballast and DBD-lamp are necessary or at least separate connections between the cooling circuit of the ballast and the DBD-lamp are necessary. Especially by having a liquid as cooling agent for the cooling device, accident sensitive and/or inexpedient hose connection and/or pipe joints between the lamp and the driver are necessary or the pipes and/or hoses have to be connected to an external supply. In applications, where several DBD-lamp-ballast-systems are needed, as mentioned before, a high effort has to be done, to connect all cooling lines/circuits to that external supply.

It is an object of the present invention to provide a combination of ballast and lamp, especially DBD-lamp, which does not need any additional connections or lines, like is electrical or cooling lines, whereby an easy and effortless installation of the lamp-ballast-system can be realized.

This issue is addressed by a lamp-ballast-system for generating and/or emitting a radiation of ultraviolet (UV-)-light comprising a lamp, especially a DBD-lamp having means for electrical contacting and/or electrical supply, and a ballast having a housing accommodating at least a high-voltage part and a lamp support, connectable to and supplying the lamp at least with electricity, whereby the electrical connection between the lamp and the ballast is arranged cable-free and/or a cooling circuit for supplying a cooling agent to the system is completely integrated.

A lamp according to this invention can be any lamp but preferably is a electrodeless lamp, where the electrical energy is supplied via capacitive or inductive contacting and is more preferably a dielectric barrier discharge (DBD)-lamp. In particular lamps according to the present invention do not have a base housing or a base socket. Such lamps or DBD-lamps usually comprise an outer part and an inner part. The outer part comprises the envelope of the inner part, whereby the inner part comprises the means for generating the radiation of the DBD-lamp. The inner part of a DBD-lamp according to this invention is structural arranged from the inside to the outside as follows:

The heart of the DBD-lamp is the discharge gap with the filling. The filling is preferably made up of a single gas, taken from the group of noble gases, or of a gas mixture, where the single components are taken from the group of noble gases and from the group of halogens. The discharge gap is formed by surrounding dielectric walls. At their outer surfaces the dielectric walls have corresponding electrodes for providing the energy to initiate a gas discharge inside the discharge gap and thus for generating the desired radiation, preferably excimer radiation. Both electrodes can be in direct, mechanical contact to the outer surfaces or at least one of them is not in direct contact and the power supply takes place via an intermediate medium, like water.

In the majority of cases two electrodes or two groups of electrodes are used: one electrode, also called active or "hot" electrode, or one group of electrodes is connected to the high voltage output of the driver/ballast and the other electrode or group of electrodes is connected to ground potential. The dielectric walls of the lamp can be additionally covered or coated at their inner surfaces with a phosphor or a luminescent layer for converting/shifting the spectrum of the radiation generated inside the discharge gap towards higher wavelengths.

The material for the dielectric walls is selected from the group of dielectric materials, preferably quartz glass. The material for the dielectric walls have to be arranged such, that the radiation generated inside the discharge gap can pass at least a part of the outer dielectric wall for applying the radiation to the environment/surroundings for treatment. Each of the walls has an inner and an outer surface. The inner surface of each wall is directed to and facing the discharge gap. The distance between the inner surface and the outer surface of one wall defines the wall thickness, which in some special cases can vary. At the outer surfaces or near the outer surfaces the electrodes are applied at/on the walls. They provide the energy in form of electricity for initiating the gas discharge inside the discharge gap and thus generating the desired radiation. For applying the radiation, the electrode at/on the outer wall—the second electrode—has to be arranged such, that radiation from the inside can pass the electrode. Thus said second electrode preferably is arranged as a grid, especially when that second electrode is arranged adjacent on the outer surface of the outer wall. In that case, in that the electrode is spaced to the outer surface of the outer wall, for example in the case of water treatment, the electrode can be of any suitable material for providing electricity in the corresponding environment.

The lamp may have any arbitrary shape, especially elliptic or oval instead of circular cross section, or flat shaped lamps. Preferably the lamp geometry is selected from the group comprising flat lamp geometry, coaxial lamp geometry, dome-shaped lamp geometry, a planar lamp geometry and the like. By this geometry the lamp can be applied with existing surroundings without adapters or additional modification. For industrial purposes coaxial DBD-lamps with relatively large diameters compared to the diameter of the discharge gap or the distance between the inner surfaces of the corresponding inner and outer wall or dome-shaped coaxial lamps are preferably used, to achieve a lamp, which is easy to produce and comprises a large effective area and a high mechanical stability.

The lamp-ballast-system further comprises a ballast or driver, which supplies the lamp with energy and therefore contains a suitable electrical topology. The driver usually comprises a housing, in which also a high voltage part of the ballast is arranged in. For realising a cable-free system, the ballast further comprises a lamp-support also housed in said housing. The housing of the ballast may have any arbitrary shape; possible material choices are: metallic housing, preferably with an electrical connection to safety ground, or insulating housing especially for low-power applications, requiring safety insulation. Preferably the housing is protected against penetration by humidity for example by means of hermetic sealing. If openings towards the active part of the ballast are required for cooling or maintenance purposes, a conformal protection coating on the conductive parts of the ballast, that is especially the high voltage part, can be applied. The high voltage part of the ballast is electrically insulated against the rest of the driver. Standard high-voltage insulation techniques are used to realize the required insulation strength.

A connection between the output stage and the lamp, more precisely the means for electrical connection like an active electrode of the lamp can be easily realized if the hot electrode is of the rod type possessing a kind of plug at one end.

As mentioned earlier, the lamp, preferably a DBD-lamp comprises usually at least one means for electrical contacting or an electrical supply cooperating with said lamp support, for example an active electrode, preferably in form of a rod, a coil, a mesh, a conductive coating/painting on the lamp envelope and the like. The active electrode can be in direct, mechanical contact with the lamp envelope or can be located in some distance from the lamp envelope. In the second case, the power supply takes place via an intermediate medium, like water.

A suitable material for manufacturing said active electrode is any conductive material, preferably metal. In case that the active electrode is of the rod type thus rod is used to supply the high-voltage output of the ballast to the lamp along the axis of the lamp. If a cooling agent of sufficient electrical conductivity is used, the rod may also be fabricated at least partially from electrically insulating material or the rod is made of metal with an at least partially insulating layer. As an option, an insulating or bad conducting rod can be supplied with a metallic coating, to enhance electrical conduction along the axis of the rod. The active electrode, which can be made in form of a rod, extends into the outer surrounding of the driver/ballast and is in direct contact with the high-voltage part of the ballast, thus an electrical contacting of the (DBD)-lamp is realized without additional cabling.

As an option the active electrode fulfils at least two functions in parallel: supply of potential to the lamp, and inlet or outlet of the cooling agent (if a cooling circuit is integrated). Therefore the active electrode is preferably of rod type and more preferably of hollow rod type, so that the cooling agent can flow through the hollow rod. However, if an inner cooling by forced liquid circulation is not required, the rod can be fabricated of full material. This is feasible in case of lamps with low power density in terms of electrical input power to lamp versus the lamp surface area. A rule-of-thumb threshold value for low power density is about 1 W/cm$^2$. In such cases, natural convection of the cooling agent may be sufficient. Additional pumps or forced convection aids are not required in this case.

In some cases the hollow structure of the metallic rod can be eliminated at all, first, if the cooling agent circulates by natural convection or second if the cooling agent has sufficient electrical conductivity to avoid heating above the boiling point, due to the lamp current, resulting into power dissipation from the electrical resistance of liquid.

A hollow version of the rod is only required if forced cooling agent circulation is needed over the full length of the lamp. In a practical situation, the temperature rise of the lamp may also be limited by means of natural convection of the cooling agent, the application of heat sinks along the outer surface of the (DBD-) lamp, and/or by heat sinks applied to the face(s) of the lamp. A hollow rod may be used either as inlet or outlet of the cooling agent, depending of the direction of circulation. Openings along the rod may either be singular or distributed along the axis of the rod.

As mentioned before, a cooling pump integrated into the driver/ballast and/or the lamp can be necessary for forced liquid cooling. Alternatively an open cooling system can be used, with inlet and outlet openings in the driver and/or lamp housing. In case of an open cooling system, several ballasts can be chained in series or connected in parallel, to make use of a central cooling supply unit.

According to the present invention, the circulation of a cooling agent inside the ballast can also be used to dissipate the heat generated by the ballast itself.

Another option is given in the special case of using a DBD-lamp for treatment of liquids in a container of reactor system. In this application, the inner cooling circuit can be fed from the outer process liquid. Potential advantages are: no secondary cooling agent and circulation loop required, and easy maintenance of the system. Inlet and outlet for the inner cooling agent can also be located on the two faces of the lamp.

The ballast comprises a lamp-support which realizes a direct contact between lamp and ballast. This lamp-support is also arranged as a mechanical support for mounting lamp and ballast together. The lamp-support can have different shapes, depending on the way the (DBD-) lamp is shaped at the mounting side. One or several openings for the cooling agent may be required, and the support is open towards the high-voltage output stage of the ballast, and the part of the (DBD-) lamp, which comprises the active electrode.

Optional at least one heat sink for dissipating the heat, which is generated inside the ballast and/or in the (DBD-) lamp, can be arranged at the lamp-ballast-system. This heat sink could be realized in many ways, for example as external heat sink. A closed cooling circuit or loop picks up all excess heat from ballast and/or from the inside of the lamp. By shaping the liquid pipes along the external heat sink(s), the temperature rise in lamp and/or ballast is limited.

Other possible external heat sinks are: the process liquids, for example if the process liquid is used as cooling agent or if the cooling agent is piped through the process liquid; external convection cooling; or external liquid cooling like heat exchanger.

According to the present invention, the ballast—with or without cooling circuit—can also be integrated inside the outer lamp envelope, preferably in case the lamp is of the coaxial type provided the available volume and dimensions match with the volume/space requirements for ballast and the other parts of the system. The main advantages are obvious: space savings—lamp and the ballast, and inner cooling are available as one integral unit, and electrical insulation of the high voltage part of ballast and lamp against the outer world is given by the bulb of the lamp.

One advantage of the present invention is, that by having no additional cabling or lines, especially electrical lines between ballast and lamp there are no additional capacitive or resistive loads of the ballast which usually exist by having cabling. Furthermore no additional electromagnetic disturbance due to the cabling exists. The risk of safety loss due to high-voltage cabling is reduced and/or at least nearly eliminated and the costs for cabling suitable for high-voltage and for appropriate connections are much lower.

Preferably the electrical connection between lamp and ballast is realized such, that the ballast is in direct contact to the active electrode and the ground electrode or only to the active electrode. This can be realized in several ways. One way is to bring the housing of ballast or driver in direct contact to the lamp. The lamp can be arranged adjacent to the housing or even at least partly extend into the housing of the ballast, such that lamp or lamp envelope and ballast housing at least partly penetrate each other. As well the driver or ballast can be arranged at least partly integrated into the lamp. In case of a coaxial DBD-lamp the ballast could be arranged inside the inner tube of the coaxial structure.

To realize a direct contact it is preferably that the connections between the lamp and the driver and/or between the high-voltage part of the driver and the means for electrical contact or the active electrode of the lamp are realized by the group of screw fittings or plug connection couplings comprising bayonet couplings. The connection serves on the one hand as mechanical connection and parallel on the other hand as electrical connection. By this connection a direct contact between ballast and lamp in a way mentioned before as well as a mechanically mounting is realized. This easy to realize connection makes the lamp-ballast-system more compact and more easily to install in several applications, where a lamp-ballast-system is applied.

During high power operation it is normally necessary to control the temperature of the lamp as well as the driver. To control and regulate the temperature at least one cooling device or cooling system is needed for the lamp-ballast-system. The cooling device can be an open cooling circuit; this is with external connections or a closed cooling circuit, with no external connections. It is favourable, that a cooling system or a cooling circuit for supplying a cooling agent is integrated, preferably completely integrated in the lamp-ballast-system. Preferably the cooling circuit is completely integrated into the lamp-ballast-system, so that no external connections have to be done. The integrated cooling circuit can control the temperature of the lamp, the ballast, or both. This enables a compact arrangement of the lamp-ballast-system as well as an easy to install system, especially in applications where several lamp-ballast-systems are needed. The cooling circuit or cooling device preferable contains a heat sink, a cooling agent, a cooling pump, and cooling lines. The cooling agent can be any suitable fluid such as forced air as well as water.

Preferably the electrical contact between the high-voltage part of the driver and the lamp is realized by a rod electrode cooperating with a lamp-support, extending from the lamp into the driver housing, which preferably is held by a high-voltage part of the ballast. By this the means for electrical contact are easy to realize.

To achieve a suitable cooling either for the lamp or the ballast or both, the cooling circuit or the cooling system is arranged at least partly in the lamp and/or at least partly in the ballast.

As mentioned before the cooling circuit comprises an integrated pumping system and integrated cooling lines. This enables a closed cooling circuit.

Preferably the integrated pumping system is located in the housing of the ballast. To arrange the cooling lines in a compact way, the lamp-ballast-system has several feed-through paths. Preferably is therefore, that at least one feed-through path is arranged in the rod electrode, the part of the (DBD) lamp, which comprises the active electrode, the lamp-support, and/or the housing. These feed-through paths can be used to integrate the cooling line(s) in a compact manner. Preferably at least one integrated cooling line is integrated in the feed-through path of the rod electrode, the high-voltage part, the lamp-support, and/or the housing.

Advantageously the cooling system and/or the cooling circuit is arranged as an open cooling system for enabling a connection of multiple lamp-ballast-systems in parallel and/or in series. By this open structure several lamp-ballast-systems could be coupled via one cooling system so that only one central cooling circuit is realized.

The cooling agent flowing through said cooling system can be an separate cooling agent in case of an closed cooling circuit or can be an internal cooling agent in case of an open cooling system taken e.g. from the process water of the application, said lamp-ballast-system is used in. By the later cooling system, that is the open cooling circuit, no additional cooling agent is necessary. The cooling agent for the cooling circuit of the lamp-ballast-system can simply be taken from the existing cooling unit of the application the lamp-systemballast is used in. In the same way the cooling agent can be directed to the cooling unit of the application.

By having a lamp-ballast-system according the present invention, a very compact and easy to handle lamp-ballast-system is realized. This system can be used in many applications or systems.

Preferably the lamp-ballast-system can be incorporated in a system and being used in one or more of the following applications: fluid and/or surface treatment of hard and/or soft surfaces, preferably cleaning, disinfection and/or purification; liquid disinfection and/or purification, food and/or beverage treatment and/or disinfection, water treatment and/or disinfection, wastewater treatment and/or disinfection, drinking water treatment and/or disinfection, tap water treatment and/or disinfection, production of ultra pure water, reduction of the total organic carbon content of a liquid or a gas, gas treatment and/or disinfection, air treatment and/or disinfection, exhaust gases treatment and/or cleaning, cracking and/or removing of components, preferably anorganic and/or organic compounds, cleaning of semiconductor surfaces, cracking and/or removing of components from semiconductor surfaces, cleaning and/or disinfection of food supplements, cleaning and/or disinfection of pharmaceuticals. This list shows the large variety of applications a lamp-ballast-system according to the invention can be used, whereby the installing of that system is easy to handle.

These and other aspects of the invention will be apparent from and elucidated with reference to the embodiments described hereinafter.

Figure 1:
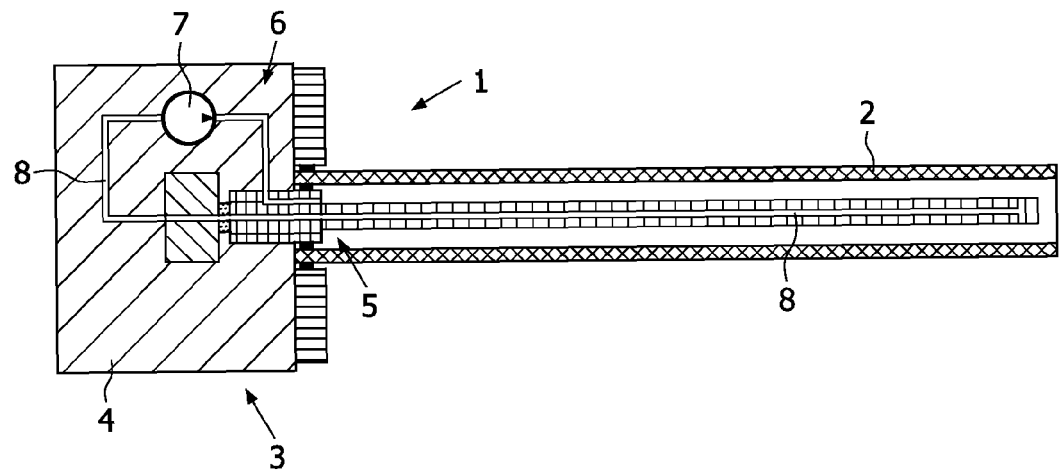
FIG. 1 shows schematically in a longitudinal sectional view a lamp-ballast-system with a coaxial DBD-lamp and a ballast arranged adjacent to the lamp.

FIG. 1 shows a lamp-ballast-system 1 including a lamp 2 and ballast 3. In FIG. 1 the lamp 2 is a dielectric barrier discharge or DBD-lamp. This DBD-lamp is of the coaxial type, whereby at one end of the coaxial lamp envelope the ballast 3 is arranged adjacent to the DBD-lamp. The ballast 3 comprising a high-voltage part and a lamp-support for supporting the lamp 2 is accommodated in a housing 4. The electrical connection 5 between lamp 2 and ballast 3 is realized by said lamp support cooperating with said lamp 2, also accommodated in the housing 4. This lamp-support is arranged as a mechanical support as well as an electrical support for mounting and/or coupling both, lamp 2 and ballast 3 together. The lamp support in this FIG. has several openings. The lamp-support is open towards the high-voltage output stage of the ballast, and the part of the DBD-lamp comprising the active electrode or in general terms the means for electrical contact. The active electrode is made in form of a metallic hollow rod. The metallic rod is used to supply the high-voltage of the ballast along the axis of the lamp. It extends into the driver housing and is in direct contact with the high-voltage part of the ballast, without any additional cabling. The metallic rod is formed as a hollow rod, so that the metallic hollow rod has mainly two functions: firstly the electrical power supply from the driver to the lamp and secondly the feeding of the cooling agent. In this first embodiment a closed cooling circuit 6 is integrated in the lamp-ballast-system 1. The cooling circuit 6 containing the cooling agent comprises a pumping system 7 and at least one cooling line 8.

Figure 2:
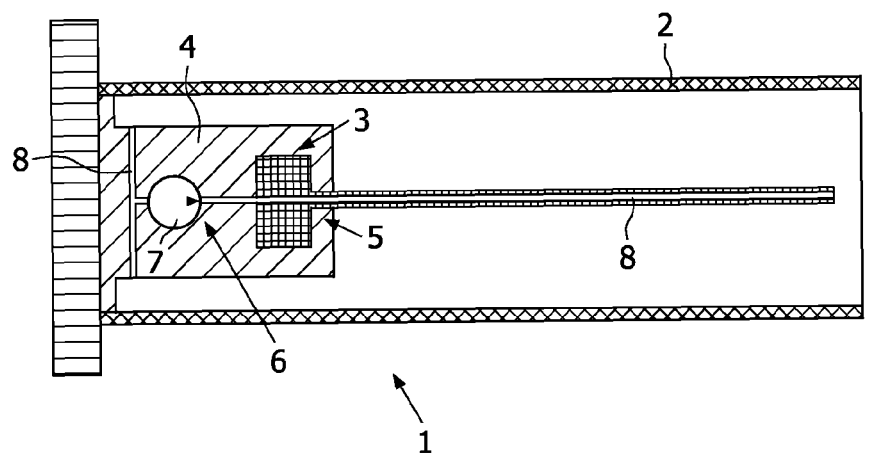
FIG. 2 shows schematically in a longitudinal sectional view a lamp-ballast-system with a DBD-lamp and a driver, whereby the driver and a cooling unit are included into the inner volume of the DBD-lamp.

FIG. 2 shows a lamp-ballast-system 1 with a coaxial DBD-lamp and a driver or ballast 3, whereby the ballast 3 and a cooling circuit are included into the inner volume of the DBD-lamp. As is FIG. 1 the lamp-ballast-system comprises a lamp 2, more precisely a DBD-lamp, and ballast 3 accommodated into a housing 4. In this embodiment the housing 4 and thus the ballast 3 is completely arranged inside the lamp 2. Again the lamp-ballast-system comprises a cooling circuit 6, here a closed cooling circuit 6.

LIST OF REFERENCE NUMBERS 1 lamp-ballast-system
2 (DBD-) lamp
3 ballast
4 housing
5 electrical connection
6 cooling circuit
7 pumping system
8 cooling line(s)

The invention claimed is:

1. A dielectric barrier discharge (DBD)-lamp-ballast-system comprising:
   a lamp having means for electrical contacting, and
   a ballast having a housing accommodating at least a high-voltage part and a lamp support, connectable to and supplying the lamp at least with electricity, the electrical connection between the lamp and the ballast being arranged cable-free; and
   a completely integrated cooling circuit for supplying a cooling agent.

2. Lamp-ballast-system according to claim 1, wherein the electrical connection is realized such that the ballast is in direct contact to the lamp.

3. Lamp-ballast-system according to claim 1, wherein the cooling circuit is arranged at least partly in the lamp and at least partly in the ballast.

4. Lamp-ballast-system according to claim 1, wherein the electrical contact between the high-voltage part of the ballast and the lamp is realized by a rod electrode extending from the lamp into the housing.

5. Lamp-ballast-system according to claim 1, wherein the cooling system and/or the cooling circuit comprises an integrated pumping system and integrated cooling lines.

6. Lamp-ballast-system according to claim 5, wherein the integrated pumping system is located in the housing.

* * * * *